United States Patent
Deshpande et al.

(10) Patent No.: US 10,568,846 B2
(45) Date of Patent: Feb. 25, 2020

(54) BETACRYPTOXANTHIN COMPOSITIONS, PROCESSES FOR PREPARATION AND USES THEREOF

(71) Applicant: OmniActive Health Technologies Limited, Mumbai (IN)

(72) Inventors: Jayant Deshpande, Charlottetown (CA); Abhijit Bhattacharya, Morristown, NJ (US); Vijaya Juturu, Morristown, NJ (US); Khadija Ghanam, Charlottetown (CA); Vandita Srivastava, Pune (IN); Vallabh Mulay, Pune (IN)

(73) Assignee: OmniActive Health Technologies Limited, Mumbai (IN)

( * ) Notice: Subject to any disclaimer, the term of this patent is extended or adjusted under 35 U.S.C. 154(b) by 295 days.

(21) Appl. No.: 15/140,063

(22) Filed: Apr. 27, 2016

(65) Prior Publication Data

US 2016/0310442 A1    Oct. 27, 2016

(30) Foreign Application Priority Data

Apr. 27, 2015   (IN) .......................... 1675/MUM/2015

(51) Int. Cl.
| | | |
|---|---|---|
| *A61K 36/81* | (2006.01) | |
| *A61K 31/045* | (2006.01) | |

(52) U.S. Cl.
CPC ............ *A61K 31/045* (2013.01); *A61K 36/81* (2013.01); *A61K 2236/00* (2013.01)

(58) Field of Classification Search
None
See application file for complete search history.

(56) References Cited

U.S. PATENT DOCUMENTS

| 7,863,241 B2 | 1/2011 | Cochrane | |
|---|---|---|---|
| 8,021,698 B2 | 9/2011 | Showalter et al. | |
| 8,673,370 B2 * | 3/2014 | Showalter | A61K 9/0019 424/725 |
| 2008/0070980 A1 * | 3/2008 | Eichinger | A23L 2/38 514/458 |
| 2011/0282083 A1 | 11/2011 | Reilly et al. | |
| 2012/0107380 A1 | 5/2012 | Tuinstra et al. | |
| 2012/0245122 A1 | 9/2012 | Jouni et al. | |
| 2014/0086986 A1 | 3/2014 | Todd, Jr. et al. | |

FOREIGN PATENT DOCUMENTS

| EP | 1748705 | 2/2007 |
|---|---|---|
| WO | 2005110122 | 11/2005 |
| WO | 2008023283 | 2/2008 |
| WO | 2014115037 | 7/2014 |
| WO | 2014186680 | 11/2014 |

OTHER PUBLICATIONS

Registry entry for beta-cryptoxanthin (RN 472-70-8—entered in STN on Nov. 16, 1984—accessed Jul. 19, 2018).*
International Search Report and Written Opinion, issued in the corresponding PCT application No. PCT/IB32016/052401, dated Aug. 22, 2016, 8 pages.
Liu et al., "β-Cryptoxanthin Supplementation Prevents Cigarette Smoke-Induced Lung Inflammation, Oxidative Damage, and Squamous Metaplasia in Ferrets", Cancer Prev Res, vol. 4, No. 48, Aug. 2011, 13 pages.
Wang, Xiang-Dong, "Role of SIRT1 in Lung Cancer Prevention by Beta-Cryptoxanthin", Grant Proposal Publication, Tufts University, Boston, available at http://grantome.com/grant/NIH/R21-CA176256-01A1, Jun. 2016.
Iskandar et al., "β-Cryptoxanthin Restores Nicotine-Reduced Lung SIRT1 to Normal Levels and Inhibits Nicotine-Promoted Lung Tumorigenesis and Emphysema in A/J Mice", Cancer Prev Res (Phila)., Author manuscript, Apr. 1, 2014, pp. 1-18.

* cited by examiner

*Primary Examiner* — Susan Hoffman
(74) *Attorney, Agent, or Firm* — Hamre, Schumann, Mueller & Larson, P.C.

(57) ABSTRACT

Compositions are described that include a betacryptoxanthin extract, rich in trans-betacryptoxanthin, which are prepared by a cost and time effective process and are for use in methods of enhancing cardio-respiratory fitness for physical performance and exercise endurance and to maintain healthy lung function. Betacryptoxanthin extract is prepared by a cost and time effective process of saponification and column chromatography, in which saponification cycle time, solvent amount, column separation time and silica amount are reduced, thus making it industrially viable. Betacryptoxanthin compositions increase exercise time, endurance performance, and lung capacity and maintain healthy lung and cardiovascular function during such physical activities. The compositions also improve physical performance, attenuate muscle fatigue, and enhance aerobic respiration utilization capacity. The compositions are safe for consumption, and can be employed for enhancing cardio-respiratory fitness when administered in an effective amount.

2 Claims, 1 Drawing Sheet

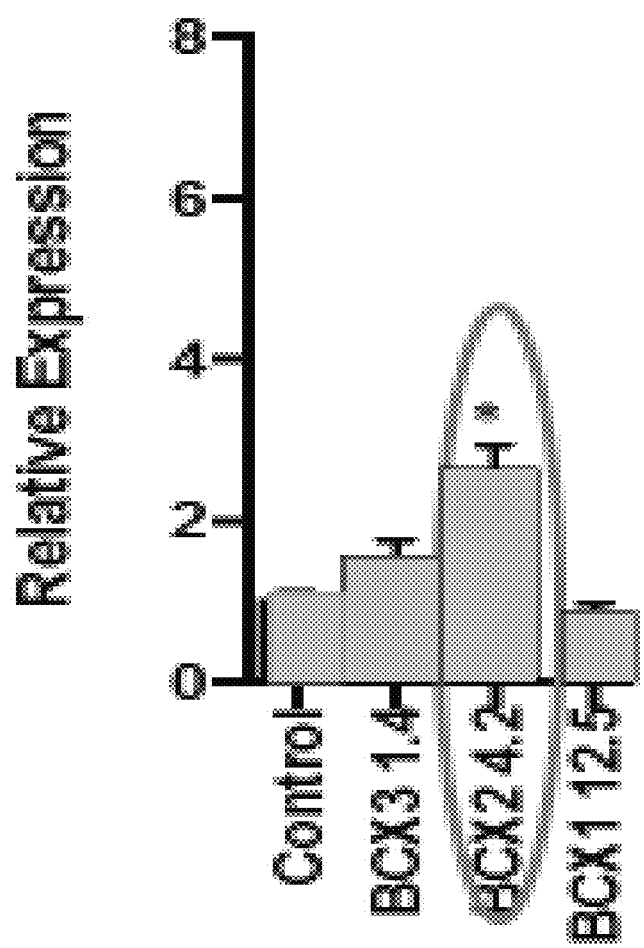

BETACRYPTOXANTHIN COMPOSITIONS, PROCESSES FOR PREPARATION AND USES THEREOF

FIELD

Compositions including betacryptoxanthin extract are described herein, and are useful for enhancing cardio-respiratory fitness for physical performance and exercise endurance and can help maintain healthy lung function. More particularly, betacryptoxanthin compositions as described herein are prepared by a cost and time effective process, and can be administered in an effective amount to exercising subjects to enhance cardio-respiratory fitness. The compositions herein include betacryptoxanthin extract formulated using at least one more nutrient and/or suitable excipient to form suitable dosage forms which can be used for pharmaceutical and nutraceutical applications. Betacryptoxanthin extract is prepared from paprika pods and paprika oleoresin, by an improved process of saponification and column chromatography, in which saponification cycle time, solvent amount, column separation time and silica amount are reduced, thus making it a cost and time effective process, which is industrially viable. Betacryptoxanthin compositions herein, when administered in an effective amount, increase exercise time, endurance performance and lung capacity, and can maintain healthy lung and cardiovascular function during such physical activities. Betacryptoxanthin compositions as described herein enhance endurance performance by improving mitochondrial mass and muscle respiration. The compositions herein also improve physical performance, attenuate muscle fatigue and enhance aerobic respiration utilization capacity. The compositions herein are safe for consumption, prepared by a cost and time effective process, which is industrially viable, and can be employed for enhancing cardio-respiratory fitness when administered to exercising subjects in an effective amount.

BACKGROUND

Physical fitness of a subject is a general state of health and well-being and, more specifically the ability to perform aspects of sports, exercise, or other routine physical activities. Fitness is generally achieved through correct nutrition, moderate to vigorous physical activity or exercise, and rest. It is a set of attributes or characteristics seen in people and which relate to the ability to perform a given set of physical activities. Earlier, fitness was linked to the capacity to carry out the day's activities without undue fatigue. However with changes in lifestyle physical fitness is now considered a measure of the body's ability to function efficiently and effectively in work and leisure activities, to be healthy, to resist diseases due to sedentary lifestyle, and to meet emergency situations. When fitness is linked to sports activities, it has five common elements—strength, speed, endurance, flexibility, and skill. The relative contributions of each of these to the specific fitness demands of different sports are, of course, not equal. To a certain extent skill can compensate for poor fitness, but improved fitness allows skillful sportspersons to extend their performance by delaying the onset of fatigue and thus, endurance plays important role in determining a subject's fitness.

Fitness for exercise or sports related activities can be of two types, cardiovascular and cardio-respiratory. Cardiovascular fitness is the ability of the heart and lungs to supply oxygen-rich blood to the working muscle tissues and the ability of the muscles to use oxygen to produce energy for movement. Cardio-respiratory fitness refers to the ability of the circulatory and respiratory systems to supply oxygen to skeletal muscles during sustained physical activity. Thus, cardio-respiratory fitness can be linked to endurance of a subject during prolonged exercise during sports, or physical activities.

A person's ability to deliver oxygen to the working muscles is affected by many physiological parameters, including heart rate, stroke volume, cardiac output, and maximal oxygen consumption. Regular exercise improves the respiratory system by increasing the amount of oxygen that is inhaled and distributed to body tissue. Cardio-respiratory fitness can reduce the risk of heart disease, lung cancer, type 2 diabetes, and stroke, and can help to improve lung and heart condition, and can increase overall wellbeing.

Although different types of aerobic and anaerobic exercises help to enhance cardio-respiratory fitness, a balanced diet, based on essential nutrients such as carbohydrates, proteins, vitamins, and minerals can enhance exercise capacity and endurance. Carotenoids such as betacryptoxanthin [BCX], which are considered a provitamin A, are known for their effects as an antioxidant and also in the treatment of inflammatory arthritis. It is present in many fruits and vegetables. BCX is a carotene and helps protect cells from free radical damage. By protecting cells from free radicals and by reducing free radical activities, it may prevent many dangerous diseases and conditions. Many references deal with different health applications of betacryptoxanthin in humans and animals.

U.S. patent application publication 20120245122A1 relates to a method for improving bone health in a subject comprising administering to the subject a carotenoid blend comprising lycopene, beta-carotene, betacryptoxanthin and combinations thereof.

PCT application WO2008023283A2 describes an esterified xanthophyll composition comprising cryptoxanthin and a method of treating breast, colon, lung, skin, cervix and ovaries cancers, as well as for treatment of cardiovascular disease, prevention of cataract and macular degeneration, as agent for the absorption of harmful ultra-violet light from the rays of the sun and quencher of photo-induced free radical and reactive oxygen species.

European patent application EP1748705 describes the use of betacryptoxanthin in the manufacture of a composition for promoting an increased protein formation and/or prevention of protein loss in human or an animal, wherein the composition is for promoting an increased protein formation in sports and workout activities.

U.S. patent application publication US20120107380 describes a method for producing a xanthophyll-enriched product from a xanthophyll ester source, wherein the xanthophyll ester is selected from zeaxanthin, lutein, beta-cryptoxanthin, astaxanthin, capsanthin, capsorubin, and mixtures thereof. This xanthophyll-enriched product is micro-encapsulated as a nutritional supplement and used for the treatment or the prevention of human or animal diseases including cancer-related diseases, cardiovascular diseases and inflammatory disorders.

U.S. Pat. No. 8,021,698B2 describes a nutritional supplement including betacryptoxanthin which is used to maintain cardiovascular health by lowering blood pressure, preventing high, elevated blood pressure and/or maintaining healthy blood pressure.

U.S. Pat. No. 7,863,241 describes a liquid or aerosolized composition comprising a lung surfactant polypeptide, a protease inhibitor and anti-oxidants in combination with carotenoid compounds such as leutein, zeaxanthin, cryptoxanthin, violaxanthin, carotene diol, hydroxycarotene, hydroxylycopene, alloxanthin and dehydrocryptoxanthin, for treating pulmonary conditions and or reducing the negative effects of pulmonary inflammation.

Liu C et al (Cancer Prev Res, 2011 August; 4(8):1255-66) relates to evaluation of effects of betacryptoxanthin supplementation on cigarette smoke-induced squamous metaplasia, inflammation, and changes in protein levels of proinflammatory cytokine (e.g. tumor necrosis factor alpha (TNFα)) and transcription factors (e.g. nuclear factor kappa B (NF-κB) and activator protein-1 (AP-1)), as well as on smoke-induced oxidative DNA damage (e.g. 8-hydroxy-2'-deoxyguanosine (8-OHdG)) in the lung tissue of ferrets. Betacryptoxanthin significantly decreased smoke-induced lung squamous metaplasia and inflammation. BCX also substantially reduced smoke-elevated TNFα levels in alveolar, bronchial, bronchiolar, and bronchial serous/mucous gland epithelial cells and in lung macrophages.

A study by Wang Xiang (NIH 2014 R21 CA) suggested that increased dietary intake or higher blood levels of betacryptoxanthin (BCX) is strongly associated with a reduced risk of lung cancer in current smokers. It was hypothesized that BCX targets silent mating type information regulation 2 homolog) 1 (SIRT1) signaling pathway as its chemopreventive action. Importantly, BCX treatment restored nicotine-reduced lung SIRT1 protein to normal levels and inhibited both nicotine-induced emphysema and nicotine-promoted lung tumor development.

Iskandar A R et al (2013 April; 6(4):309-20) describes the effect of BCX as a preventive agent against emphysema and lung cancer with SIRT1 as a potential target.

SUMMARY

Even though the references above discuss the effect of betacryptoxanthin in bone health, lung cancer treatment, and inflammatory conditions, and in management of ill effects of smoking in lungs, there is no discussion about the use of betacryptoxanthin compositions for enhancing exercise performance and endurance and maintaining lung and cardiovascular health related to exercise. Further none of the references above discuss the evaluation of betacryptoxanthin for its protective effect on lung health through a mechanism such as for example reduction of oxidative stress markers, or discuss the improvement of lung function as well as cardiovascular function, thus resulting in improved exercise endurance and cardio-respiratory function.

Further prior processes for producing beta-cryptoxanthin have several limitations. While natural sources of betacryptoxanthin are available, extracts have thus far been produced only in enriched form in fruit drinks such as tangerine, satsuma orange, and persimmon. The use of a biotechnological route for producing betacryptoxanthin is still in preliminary development and has thus far been limited to laboratory scale production with poor yields. The synthetic approach gives a mixture of betacryptoxanthin and a considerable amount of impurities such as alpha-cryptoxanthin, which is most likely zeinoxanthin (a non-provitamin A), along with un-reacted anhydroluteins and zeaxanthin. Applying other processes of the literature, the separation of beta-cryptoxanthin is complex, involves multiple steps, and is not commercially feasible. Thus, a need exists for an alternate preparation process for a betacryptoxanthin composition, which is rich in trans-betacryptoxanthin, and which would be cost and time effective and therefore industrially viable.

Applicant has carried out rigorous experimentation for the preparation of betacryptoxanthin extract, compositions including betacryptoxanthin extract, and evaluation of the effect of betacryptoxanthin compositions in the enhancement of cardio-respiratory fitness, when the betacryptoxanthin composition is administered in an effective amount to a subject who is exercising.

In an embodiment, a betacryptoxanthin composition herein includes an extract enriched in trans-betacryptoxanthin. In an embodiment, the extract is prepared from paprika pods or oleoresin using a process including polar and non-polar solvents.

In an embodiment, the process includes two steps, saponification and column separation. In an embodiment, an oleoresin is saponified using a polar solvent(s) and alkali at ambient to elevated temperature conditions. A saponified mass is extracted with a non-polar solvent to obtain a concentrated extract, which is purified by column chromatography to obtain a content of at least 75% trans-betacryptoxanthin by weight of the extract.

In an embodiment, the process described herein significantly reduces saponification time and column separation time, and is also cost effective as less solvent and silica gel are used as compared to previous processes. In an embodiment, the process described herein, can obtain betacryptoxanthin from column separation does not require a further purification step, and thus it further saves time of an additional step(s). The extract thus obtained is used as such or formulated into a suitable composition such as beadlets, tablets, capsules, oil suspension, and the like by employing one or more nutrients and pharmaceutically or nutraceutically acceptable excipients such as carrier, binder, solubilizer, stabilizer, coating, lubricant.

Betacryptoxanthin compositions herein are evaluated for their effect on enhancing physical performance and maintaining healthy lungs and cardiovascular functions. Betacryptoxanthin compositions described herein increase exercise performance by enhancing mitochondrial mass and muscle respiration. The compositions also exhibit positive effect on E-Cadherin (ECAD) gene expression in primary bronchial epithelial cells and manage inflammatory markers, thus protecting the lungs and improving lung capacity for exercise endurance by improving forced expiratory volume (FEV1) and forced vital capacity (FVC) parameters, when administered to a subject in an effective amount.

Forced vital capacity (FVC) and Forced expiratory volume (FEV) are parameters measured in spirometry, which is a pulmonary function test. Spirometry is used to measure or assess lung function, specifically the amount (volume) and/or speed (flow) of air that can be inhaled and exhaled. Pulmonary function tests include the forced expiratory volume (FEV1), which is the amount of air exhaled in one second, and the forced vital capacity (FVC), which is the maximum amount of air that can be exhaled in a single breath. Both FVC and FEV1 are measured with the help of a spirometer. Repeated periodic exercise helps in improving lung functions, especially FEV1 and ratio of FEV1/FVC. Periodic measurement of FEV1 can help in generating awareness regarding lifestyle modifications, and acquiring a healthy habit of being active.

Betacryptoxanthin compositions described herein can be administered to a subject, in the form of a pharmaceutical or a nutraceutical delivery system, in the form of a dietary supplement, a dosage form or in a suitable vehicle, which is convenient for administration. The compositions herein can be administered in the form of powders, granules, sachets, beadlets, tablets, capsules, caplets, suspensions, emulsions, solutions, energy bar, beverages, functional foods and the like.

In an embodiment, the compositions as described herein are prepared from a suitable paprika source. In an embodiment, methods herein include administering a betacryptoxanthin composition, which is administered in a dosage, such as at or about 0.001 to at or about 10 mg/kg body weight of a subject. The dosage can also vary from at or about 1.0 to at or about 9.0 mg/kg body weight or to at or about 2.0 to at or about 8.0 mg/kg body weight of betacryptoxanthin. In an embodiment, the amount of betacryptoxanthin includes, for example a betacryptoxanthin extract obtained by the process herein, and which is part of a betacryptoxanthin composition including the extract. The dosage form or dietary supplement can be administered in an effective amount, as a single dose for a single day, as a daily dose over an extended time period or specific time duration, or as a single or multiple servings during the day, based on the subject. In an embodiment, betacryptoxanthin compositions described herein contain one or more pharmaceutically and/or nutraceutically acceptable excipients, along with one or more additives such as but not limited to vitamin(s), lipid(s), carbohydrate(s), amino acid(s), trace element(s), coloring(s), flavor(s), artificial sweetener(s), natural antioxidant(s), stabilizer(s), preservative(s), and buffer(s).

In an embodiment, a betacryptoxanthin composition herein includes an extract enriched in trans-betacryptoxanthin, which is prepared by an economically viable process, which may use conventional equipment. The compositions herein are found to be effective for enhancing physical performance during exercise, sports activities, and/or routine physical activities, and also for enhancing recovery after prolonged physical activities by enhancing cardio-respiratory fitness of a subject, when administered in an effective amount.

BRIEF DESCRIPTION OF THE DRAWINGS

FIG. 1 is a bar graph showing the effect of BCX on ECAD in bronchial epithelial cells.

DETAILED DESCRIPTION

Betacryptoxanthin (BCX) compositions described herein are comprised of an extract with at least 75% by weight of trans-betacryptoxanthin, which are prepared by using polar and non-polar solvents using an industrially viable cost and time effective process. The BCX compositions including extract comprising trans-betacryptoxanthin and one or more excipients to form a suitable dosage form are useful to enhance performance during physical activities, such as exercise and sports and to maintain healthy lungs and cardiovascular function. More particularly, betacryptoxanthin compositions herein are administered in suitable dosage forms to enhance cardio-respiratory fitness of a subject by increasing exercise time, endurance performance, and lung capacity and to maintain healthy lung and cardiovascular function during such physical activities. Betacryptoxanthin compositions herein enhance endurance performance by enhancing mitochondrial mass and respiration in muscles. The compositions herein also improve physical performance, attenuate muscle fatigue and enhance aerobic respiration utilization capacity.

Betacryptoxanthin compositions herein may be obtained by human intervention and are safe for administration and are thus useful for pharmaceutical and nutraceutical applications.

The terminology 'subject' is commonly used in the specification to refer to an individual or mammal such as a human or animal under test, being treated with compositions herein.

The terminology "subject in need thereof" can include specific individuals or mammals, who need to undergo sustained physical activities, exercise or sports activities for a prolonged time, and/or who may need to have improvement in lung and cardiovascular function, to support increased energy demands of vigorous and/or sustained physical activities. Thus there is a need to have improved cardio-respiratory fitness in such subjects, in terms of protection and management of both vital body systems.

The terminology "effective amount" refers to the amount of betacryptoxanthin present in the composition. In an embodiment, this refers to the amount of the extract enriched with betacryptoxanthin, which in an embodiment is at least 75% by weight of trans-betacryptoxanthin.

The terminology "cost and time effective process" means the process in which cost and time for preparation is reduced effectively by modifying the process in which saponification time is considerably reduced along with time for separation of trans-betacryptoxanthin fraction from column chromatography. The amount of solvents used, such as hexane and acetone for column separation and the silica gel in the column, is also significantly reduced as per the process described herein. Thus the process herein is a cost and time effective process, which is industrially viable and can be used on a large scale to obtain a betacryptoxanthin extract for the betacryptoxanthin compositions herein.

The cardiovascular system is responsible for a vast set of adaptations in the body throughout exercise. It often can immediately respond to changes in cardiac output, blood flow, and blood pressure. Cardiac output is defined as the product of heart rate and stroke volume, which represents the volume of blood being pumped by the heart each minute. Cardiac output increases during physical activity due to an increase in both the heart rate and stroke volume. At the beginning of exercise, the cardiovascular adaptations are very rapid. Both heart rate and stroke volume vary directly with the intensity of the exercise performed. Cardiac output can be improved through consistent body training and exercise.

Regulation of blood flow during exercise is also a factor for consideration. During exercise, blood flow increases in order to provide the working muscle with more oxygenated blood, which can be accomplished through neural and chemical regulation. Also, chemical factors such as a decrease in oxygen concentration and an increase in carbon dioxide or lactic acid concentration in the blood promote vasodilatation to increase blood flow. Although the described adaptations in the body are significant to maintain homeostatic balance during exercise, the involvement of the respiratory system is also considered significant if not more so. The respiratory system allows for the proper exchange and transport of gases to and from the lungs while being able to control the ventilation rate through neural and chemical impulses. Thus fitness of both body systems, e.g. the lung and cardiovascular systems, is important to have enhanced endurance and performance for physical activity including normal activity and during exercise and sports and thus, performance during physical activity is interlinked with cardio-respiratory fitness.

Exercise increases the utilization of oxygen in the body, and therefore enhances the production of reactive oxygen species and impairs both enzymatic and non-enzymatic antioxidant defense systems in skeletal muscle and blood. The activity of AMP-activated protein kinase (AMPK), peroxisome proliferator-activated receptor-γ coactivator 1α (PGC-1α), nuclear respiratory factor 1 (NRF1) mitochondrial transcription factor A (TFAM), and sirtuins may play a role in the exercise-induced adaptive response. SIRT1 is a regulator of metabolism that controls the activity of key transcription factors, such as for example PGC-1α, forkhead box protein 01 (FOXO1), and tumor protein p53, which play a role in the training response. Therefore, activators of SIRT1 could have potentially beneficial effects which enhance aerobic performance. Recent studies have indicated that antioxidant supplementation led to the prevention of strenuous exercise induced oxidative injury in in-vivo studies (e.g. in rats having a high endurance capacity). Many studies have indicated that antioxidant nutrient supplementations prevented strenuous exercise-induced oxidative injury in human subjects and rats (Khanna et al. 1999).

In some embodiments, betacryptoxanthin compositions herein are administered in an effective amount to enhance cardio-respiratory fitness in a subject and/or and the beneficial effects are evaluated for exercise performance and lung capacity in a subject.

In one embodiment, compositions described herein are directed for improvement of exercise endurance and lung health by administering to a subject in need thereof, an effective amount of a composition comprising betacryptoxanthin alone or in combination with other nutrient(s) and/or with other excipient(s).

In an embodiment, compositions herein are comprised of an extract enriched with at least 75% by weight of trans-betacryptoxanthin. The compositions herein comprised of trans-betacryptoxanthin extract can be used for administration to a subject and for evaluation of its beneficial effects.

In some embodiments, compositions herein are in the form of a dosage form including, but not limited to, beadlets, microencapsulated powders, oil suspensions, liquid dispersions, capsules, pellets, ointments, soft gel capsules, tablets, chewable tablets, or lotions/liquid preparations. The composition as described herein can also be provided in a food or feed (including liquid or solid) composition. Thus, it is envisioned that suitable delivery methods include, but are not limited to, oral, parenteral, subcutaneous, intravenous, intramuscular, intraperitoneal, transdermal, intracranial, or buccal administration. Compositions comprising trans-betacryptoxanthin may include one or more suitable pharmaceutically acceptable ingredients or food grade ingredients such as, but not limited to, carriers, binders, stabilizers, excipients, diluents, pH buffers, disintegrators, solubilizers and isotonic agents.

In one embodiment, compositions herein include an extract enriched with at least 75% trans-betacryptoxanthin, along with one or more nutrients selected from the group of, but not restricted to beta-carotene, zeaxanthin, capsanthin, carotenoids, omega 3 fatty acids, vitamins and combinations thereof.

In an embodiment, the betacryptoxanthin extract can be enriched with up to 100% by weight trans-betacryptoxanthin.

The compositions herein include a "therapeutically effective amount" or a "prophylactically effective amount" of the trans-betacryptoxanthin extract. A "therapeutically effective amount" refers to an amount effective, at a dosage and for a period of time to achieve the desired therapeutic result, for example in methods of treatment or compositions for use in such methods. A therapeutically effective amount may vary according to factors such as the disease state, age, sex, and weight of the individual. A therapeutically effective amount is also one in which any toxic or detrimental effects of the composition are outweighed by the therapeutically beneficial effects. A "prophylactically effective amount" refers to an amount effective, at a dosage and for a period of time to achieve the desired prophylactic or preventive result. In an embodiment, since a prophylactic dose administered to a subject prior to or at an earlier stage of disease or a condition treatment, the prophylactically effective amount is less than the therapeutically effective amount.

In an embodiment, betacryptoxanthin compositions are prepared from suitable varieties of paprika, employing a solvent extraction process. The plant material is derived from sources including, but not limited to, fruits and vegetables. In some embodiments, the plant material is derived from capsicums. *Capsicum* is a genus of flowering plants that includes several varieties of peppers, such as but not limited to red peppers, and the word "*capsicum*" is also used interchangeably in several parts of the world when referring to peppers. The *capsicum* oleoresin described herein also includes paprika oleoresin.

In an embodiment, compositions herein are prepared from paprika pods or paprika oleoresin containing about 0.1-2% by weight of betacryptoxanthin. The remaining carotenes present include betacarotene, zeaxanthin, trans-capsanthin and trace amounts of other carotenoids. In an embodiment, a resulting extract contains a betacryptoxanthin content of at least 75% by weight. The process of preparation includes the steps of admixing *capsicum* oleoresin with a suitable solvent, saponifying the xanthophyll esters, extracting a saponified mass with a solvent, for example hexane, obtaining a concentrate which is loaded on silica gel column, eluting with a combination of polar and non-polar solvents to obtain a composition enriched with at least 75% by weight of trans-betacryptoxanthin, which can be further formulated using pharmaceutically or nutraceutically acceptable excipients and/or carriers.

In some embodiments, solvents employed in the process for preparation of betacryptoxanthin are selected from, but not limited to non-polar, semi-polar and/or polar solvents or combinations thereof. More preferably the solvents are selected from polar solvents such as but not limited to acetone, ethyl acetate, acetonitrile, ether, alcohols including aliphatic alcohols, water and the like, either alone or in combination thereof.

In certain embodiments, the aliphatic alcohol comprises a hydrocarbon fragment derived from a fatty, non aromatic hydrocarbon and is selected from the group consisting of ethanol, methanol, isopropyl alcohol, and mixtures thereof. In some embodiments, the aliphatic alcohol is ethanol.

In some embodiments, the non-polar solvent used in the process may be selected from the group of, but not limited to pentane, hexane, cyclohexane, benzene, toluene, chloroform, diethyl ether and the like or mixtures thereof. In one embodiment, the non polar solvent used herein is hexane.

In some embodiments, the alkali is a soluble hydroxide of the alkali metals, including but not limited to lithium, sodium, potassium, rubidium, or cesium. In an embodiment, the alkali is selected from the group consisting of sodium hydroxide, potassium hydroxide, and mixtures thereof. In some embodiments, the alkali is sodium hydroxide. In other embodiments, the alkali is potassium hydroxide.

According to still one more embodiment, the elevated temperature for saponification is above room temperature. In some embodiments, the elevated temperature ranges from about 65 to about 95° C., about 70 to about 90° C. about 75 to about 85° C., about 75 to about 80° C., or about 80 to about 85° C.

As per one more embodiment, suitable weight ratio of oleoresin to solvent may range from 1:0.5 to 1:20 and suitable ratio of oleoresin to alkali may range from 1:0.05 to 1:5 by weight.

In some embodiments, a process for preparing betacryptoxanthin composition includes the following steps:
1. Mixing *capsicum* oleoresin with ethanol in a suitable ratio;
2. Saponifying the oleoresin with potassium hydroxide, wherein the ratio of oleoresin to potassium hydroxide is about 1:0.25 weight/weight; adding mixed tocopherol to the mixture
3. Applying heat to the oleoresin to elevate the temperature up to reflux at about 80-85° C. and agitating the oleoresin for about 3 to 5 hours at about 80-85° C. to get a saponified mass.
4. Extracting the saponified mass with hexane and concentrating the hexane washings to obtain a concentrated mass. This mass will be used as feed for column chromatography.
5. Forming a slurry of hexane concentrated mass with silica and drying to obtain an adsorbed mass on silica, which is loaded onto a column and eluted with hexane to obtain fractions other than betacryptoxanthin;
6. Washing the column with hexane to acetone mixture and concentrating the washings to obtain an extract composition comprising at least 75% by weight of trans-betacryptoxanthin.

The process described herein is cost and time effective and industrially viable in terms of scalability and reduced cycle time. The amount of solvents used in the process are less or reduced as compared to previous processes, and the time for saponification and column separation is also significantly low or reduced as compared to previous processes. Betacryptoxanthin separated from column chromatography can avoid additional step(s) of purification, thus the process herein saves time and provides betacryptoxanthin having assay of about 12% w/w to comply with desired purity standard of betacryptoxanthin.

In an embodiment, the betacryptoxanthin extract is prepared from paprika pods and paprika oleoresin, by an improved process of saponification and column chromatography, in which saponification cycle time, solvent amount, column separation time and silica amount are reduced, thus making it a cost and time effective process.

In an embodiment, a betacryptoxanthin extract herein thus obtained is either used as such or formulated using suitable excipient to obtain a betacryptoxanthin composition.

In some embodiments, the composition herein can be formulated in a dosage form including, but not limited to, beadlets, microencapsulated powders, oil suspensions, liquid dispersions, capsules, pellets, ointments, soft gel capsules, tablets, chewable tablets or lotions/liquid preparations. The composition as described herein can also be provided in a food or feed (including liquid or solid) composition. It will be appreciated that suitable delivery methods include, but are not limited to, oral, parenteral, subcutaneous, intravenous, intramuscular, intraperitoneal, transdermal, intracranial, or buccal administration. Compositions herein comprising trans-betacryptoxanthin may include one or more suitable pharmaceutically acceptable ingredients or food grade ingredients such as, but not limited to, carrier(s), binder(s), stabilizer(s), excipient(s), diluent(s), pH buffer(s), disintegrator(s), solubilizer(s) and isotonic agent(s).

A betacryptoxanthin composition herein may be administered by oral route, in combination with an antioxidant and/or one or more other nutrients, and may use an oil vehicle for suspending the composition.

In one embodiment, betacryptoxanthin compositions, processes for their preparation, and methods of using them are directed to the improvement of cardio-respiratory fitness by increasing mitochondrial mass, muscle respiration, lung capacity and reduction in oxidative stress and inflammatory markers in lung tissues.

In accordance with embodiments herein, the following study is undertaken with an animal model to investigate the effects of BCX in rats after exhaustive exercise. Effect of BCX compositions is investigated on lipid profile, oxidative stress, antioxidant enzymes and muscle fatigue. The effect is also observed on promoting lung health and cardiovascular health in exercising rat models.

According to one embodiment, betacryptoxanthin compositions and methods herein are also used to treat and/or evaluate their effect on expression of inflammatory markers and/or oxidative stress markers. It is observed that betacryptoxanthin compositions herein and methods of use thereof reduce inflammatory markers.

In one embodiment, betacryptoxanthin compositions herein and methods of use thereof are directed to the improvement of cardiovascular health by management of a healthy lipid profile, reduction in body fat, visceral fat, and free fatty acid levels in the body.

In one embodiment, betacryptoxanthin compositions herein and methods of use thereof are directed to administering the composition in an effective amount, for example in a dose of at or about 0.001 to at or about 10 mg/kg body weight, for the improvement of physical performance, exercise endurance, lung health, lung capacity and cardio-respiratory fitness and/or to reduce oxidative stress markers in the lung tissue. In some embodiments, dose ranges can include at or about 1 mg to at or about 9.0 mg/kg body weight of betacryptoxanthin (BCX) administered to a subject. The dose ranges can also include at or about 2.0 to at or about 8.0 mg/kg body weight of betacryptoxanthin in a subject. In an embodiment, the dose ranges are evaluated in-vitro and in-vivo for effect of betacryptoxanthin on lung and cardiovascular function as a result of sustained exercise activities, sports performance or normal physical activities.

While the compositions and methods have been described in terms of illustrative embodiments, certain modifications and equivalents will be apparent to those skilled in the art and are intended to be included within the scope of the compositions and methods herein. The details and advantages of which are explained hereunder in greater detail in relation to non-limiting exemplary illustrations.

EXAMPLES

Example 1

Process for Preparation of Betacryptoxanthin Composition

Saponification:
Paprika oleoresin was mixed with ethanol in a ratio of about 0.5:1 to 1:3 weight/volume and it was saponified with potassium hydroxide employing the ratio of oleoresin to potassium hydroxide to about 1:0.1 to 1:0.5 w/w. Mixed tocopherol (1% w/w) was added with respect to oleoresin quantity. The mixture system was heated to about 80-85° C. for about 3 to 5 hours to get saponified mass.

Column Separation:

Saponified mass was extracted with hexane and the extracted mass was concentrated, which was used as 'hexane extract concentrate' feed for column chromatography. Hexane concentrate was added to silica gel to form slurry and dried to obtain an adsorbed mass on silica. This adsorbed silica was loaded in the column for separation. The column was first eluted with hexane to obtain a carotene fraction; followed by further washing with hexane to obtain a betacarotene fraction. Hexane and acetone combination was used for separation of trans-betacryptoxanthin and the fraction was concentrated to obtain an extract comprising at least about 75% by weight trans-betacryptoxanthin.

Paprika oleoresin having varying content of BCX is selected for experiment BCX1, BCX2, and BCX 3 as shown in Table No. 1. Hexane concentrate column indicates content of BCX obtained after saponification step and the last column indicates content of BCX obtained after column separation. BCX amount was determined by routine HPLC method. Dose amounts referred to in the tests hereafter refers to the amount of the BCX extract.

TABLE 1

Betacryptoxanthin (BCX) preparation steps and active contents analysis

| Experiment | Input Paprika Oleoresin % BCX | BCX content in Hexane concentrate | | BCX content in fraction obtained from Column separation | | |
|---|---|---|---|---|---|---|
| | | % Yield | % BCX | % Yield | % BCX | % Area of BCX |
| BCX1 | 0.56 | 12.86 | 3.68 | 4.54 | 10.3 | 73.64 |
| BCX2 | 0.61 | 11.44 | 4.63 | 4.27 | 11.27 | 74.5 |
| BCX3 | 0.78 | 12.2 | 5.05 | 4.02 | 14.56 | 74.79 |

Example 2

In Vitro Study in Primary Bronchial Epithelial Cell Cultures (PBEC) Lung Model

Normal Human Bronchial/Tracheal Epithelial Cells (NHBE, Lonza Walkersville Md.) were purchased and cultured in BEGM Bulletkit Media following the supplied protocol (Lonza). Cells were cultured until they were confluent and then treated overnight with betacryptoxanthin composition (BCX). Subsequently, RNA was isolated and cDNA prepared using standard protocols and real-time PCR performed for testing E-Cadherin (ECAD).

Observation:

ECAD genes showed a significant change in gene expression upon treatment with BCX. The regulation of ECAD is of note since this protein contributes to the structural and immunological function of airway epithelium through the regulation of epithelial junctions, proliferation, differentiation, and production of growth factors and proinflammatory mediators. The dose-response relationship for induction of ECAD was atypical with a peak at 4.2 µg/mL that then fell to control levels at 12.5 µg/mL. See FIG. 1 of the effect of BCX on ECAD genes in bronchial epithelial cells.

Example 3

Effect of BCX on Pulmonary Structural and Functional Changes on Skeletal Muscle Against Damage Induced by Exhaustive Exercise in Rats Animals and Exercise Protocol 8-10 male Wistar rats per treatment arm (age: 8 week, weight: 180±20 g) were housed in a controlled environment with a 12:12-h light-dark cycle at 22° C. and provided with rat chow and water ad libitum. All experiments were conducted under the National Institutes of Health's Guidelines for the Care and Use of Laboratory Animals and approved by the Ethics Committee of the Veterinary Control Institute. Following a 7-day acclimatization period, rats of both the control and exercise groups were divided into groups by matched body weight. Animals were randomly divided into the following groups and all treatments were administered daily as an oral supplement per day for 8 weeks.

| Group I, N = 7/arm | Group II, N = 7/arm |
|---|---|
| Control | Exercise |
| Control + BCX 2.5 mg/kg body weight | Exercise + BCX 2.5 mg/kg body weight |

The exercise protocols were performed on a motor-driven rodent treadmill (MAY-TME, Commat Limited, Ankara, Turkey). The treadmill equipped with an electric shock grid on the rear barrier to provide exercise motivation to the animals. All exercise tests were performed during the same time period of the day to minimize diurnal effects. The animals in the chronic exercise groups were habituated by treadmill exercise over a 5-day period such as: 1st day 10 m/min, 10 min; 2nd day 20 m/min; 10 min, 3rd day 25 m/min, 10 min; 4th day 25 m/min, 20 min and 5th day 25 m/min, 30 min. Thereafter, the animals exercised at 25 m/min, 45 min/day, 5 days per week for 8 weeks (Liu et al. 2000.) To minimize diurnal effects, all animals were exercised at the same time (09.00-12.00 hours).

Sample Collection

The rats were killed 24 h after the last exercise in the chronic exercise group (to wean the effects of acute exercise) by cardiac puncture. Within 1 min, blood samples were transferred into ethylenediaminetetraacetic acid (EDTA)-coated tubes and plasma was separated by centrifugation at 1750 g for 10 min at 48° C. Plasma samples were stored at −80° C. until the time of analysis. Lung and Muscle samples were collected and frozen at −80° C. for further analyses.

Morphological Study

The harvested lobes of lung were fixed in 4% formaldehyde solution for 72 hours. Histopathologic examination of the samples was performed in all groups. Briefly, the lung tissues from groups were embedded in paraffin and cut into a 4-μm section. The lung sections were stained with hematoxylin and eosin (H&E) solution applied to a glass slide and photographed under a light microscope (Olympus, Japan) at a magnification of 400 for morphological analysis.

Mean linear intercept (MLI) and mean alveolar number (MAN) were examined on two glass slides of each group in the same size of the field of view. Using light microscopy, MLI was determined for each region was studied on an overlay consisting of horizontal and vertical lines. All intercepts with alveolar septal number (ASN) were counted at the intersection point of the two lines in the central field of the view under microscope. The total length (L) of all the lines together was divided by the number of intercepts to obtain the mean linear intercept for the region studied. A formula is shown as MLI=L/ASN, which is used to estimate an average diameter of a single alveolus in size.

MAN determined according to alveolar number (AN) in each field of view and a square area (SA) of the field. A formula is shown as MAN=AN/SA (mm$^2$), which is an indicator for density of alveoli.

Laboratory Analyses

Plasma was used for the determination of glucose, lipid profile, cortisol, serotonin, testosterone, creatine kinase activity (CK), aspartate transaminase (AST), alanine transaminase (ALT), with an automatic analyser (Olympus). The serum lungs and muscle malondialdehyde (MDA) levels were measured by high performance liquid chromatography (HPLC) (Shimadzu). The total superoxide dismutase (SOD), catalase (CAT), and glutathione peroxidase (GPx) were measured using a commercially available assay kit (Cayman Chemical, Ann Arbor, Mich., USA) according to the manufacturer's instructions. Proteins (NF-kB, Nrf2, heme oxygenase 1(HO-1)) for pathways were analyzed by Western blot methods in muscle samples.

Histological Analysis

Samples of skeletal muscle (vastus lateralis) were collected from each rat in each experimental condition and fixed with a solution of 2% glutaraldehyde in phosphate buffer at 4° C. for 2 hours (h). Samples were treated with phosphate buffer and dehydrated in a graded series of ethanol and embedded in Epon 812 resin (Fluka, Sigma-Aldrich). From each sample, sections of 500 nm were obtained with ultramicrotome and subsequently stained with a solution of 1% toluidine blue buffered with borate. They were observed under light microscopy, and images recorded by software.

Statistical Analyses

Data is presented as mean±SEM. Sample size was calculated based on a power of 85% and a p value of 0.05. Given that assumption, a sample size of seven per treatment was calculated. Data analysis was done between control vs exercise vs control+product X vs exercise+product X. The data was analyzed using the generalized linear model (GLM) procedure of SAS (SAS Institute: SAS User's Guide: Statistics). The treatments compared between control vs exercise vs control+product X vs exercise+product X using analysis of variance (ANOVA) and student's unpaired t test; P<0.05 was considered statistically significant.

Results:

Total cholesterol and triglycerides were significantly decreased in Exercise treated rats with BCX. The compositions also decreased muscle oxidative stress and improved muscle antioxidant enzymes, in the exercising rat models. See Table No. 2.

TABLE NO. 2

Effect of BCX composition on Lipid profile

| Item | Control | Beta crypto-xanthin | Exercise | Exercise + Beta crypto-xanthin | SEM | --P-- |
|---|---|---|---|---|---|---|
| Glucose, mg/dL | 101.57 | 100.43 | 91.43 | 92.57 | 5.16 | 0.568 |
| T-C, mg/dL | 75.14$^a$ | 74.71$^a$ | 74.00$^a$ | 65.57$^b$ | 0.74 | 0.0001 |
| TG, mg/dL | 103.71$^a$ | 102.14$^a$ | 84.29$^{ab}$ | 75.57$^b$ | 3.84 | 0.0001 |

T-C: Total Cholesterol; TG: Triglycerides;.
Data are means the standard error of the mean (SEM).
Different superscripts (a-e) indicate group mean differences (p < 0.05).

TABLE NO. 3

Effect of BCX composition on muscle oxidative stress and muscle antioxidant enzyme

| Item | Control | Beta crypto-xanthin | Exercise | Exercise + Beta crypto-xanthin | SEM | --P-- |
|---|---|---|---|---|---|---|
| Lactate, mg/dL | 9.66$^b$ | 9.33$^a$ | 7.47$^b$ | 6.13$^{bc}$ | 0.29 | 0.0001 |
| Muscle MDA, nmol/mg protein | 78.84$^a$ | 65.76$^b$ | 74.16$^b$ | 53.16$^c$ | 1.77 | 0.0001 |
| Muscle SOD, U/mg protein | 0.22$^e$ | 0.38$^{bd}$ | 0.34$^d$ | 0.46$^{ab}$ | 0.02 | 0.0001 |
| Muscle GPx, U/mg protein | 143.29$^c$ | 162.71$^b$ | 155.71$^{bc}$ | 192.86$^a$ | 4.09 | 0.0001 |

MDA: Malondialdehyde; SOD: superoxide dismutase; GPx: Glutathione peroxidase.
Data are means the standard error of the mean (SEM).
Different superscripts (a-e) indicate group mean differences (p < 0.05).

Significant reduction in muscle oxidative stress MDA, decreased lactate and increased SOD and GPx levels were observed in exercise treated rats with BCX and also in control rats treated with BCX compared with control diet fed rats. See Table No. 3.

TABLE NO. 4

Effect of BCX on lung antioxidant enzymes

| Item | Control | Beta crypto-xanthin | Exercise | Exercise + Beta crypto-xanthin | SEM | --P-- |
|---|---|---|---|---|---|---|
| Lung MDA, nmol/mg protein | 97.41$^a$ | 80.82$^b$ | 91.21$^a$ | 68.63$^c$ | 1.75 | 0.0001 |
| Lung SOD, U/mg protein | 0.34$^e$ | 0.49$^c$ | 0.43$^d$ | 0.62$^b$ | 0.01 | 0.0001 |

TABLE NO. 4-continued

Effect of BCX on lung antioxidant enzymes

| | Groups | | | | | |
|---|---|---|---|---|---|---|
| Item | Control | Beta crypto-xanthin | Exer-cise | Exer-cise + Beta crypto-xanthin | SEM | --P-- |
| Lung GPx, U/mg protein | 152.43$^c$ | 170.29$^b$ | 162.57$^{bc}$ | 192.43$^{bc}$ | 3.23 | 0.0001 |

MDA: Malondialdehyde; SOD: superoxide dismutase; GPx: Glutathione peroxidase.
Data are means the standard error of the mean (SEM).
Different superscripts (a-e) indicate group mean differences ($p < 0.05$).

Significant reduction in lung oxidative stress MDA, lung SOD and GPx levels were observed in exercise treated rats with BCX and also in control rats treated with BCX compared with control diet fed rats. See Table No. 4.

BCX compositions herein, when administered in an effective amount, were found to manage lipid profile, reduce muscle oxidative stress and improve muscle antioxidant enzymes, thus reducing oxidative stress in exercising subjects, along with managing cardiovascular disease risk factors such as body lipids. The compositions also reduced lung oxidative stress and muscle oxidative stress by managing muscle and lung antioxidant enzymes. Betacryptoxanthin compositions herein, when administered in an effective amount, support healthy lung and cardiovascular function during such physical activities such as exercise, sports, or related strenuous activities. The compositions herein, when administered in an effective amount, attenuate muscle fatigue by reducing lactate content and enhance cardio-respiratory fitness for physical performance and exercise endurance and maintain healthy lung function.

The invention claimed is:

1. A method of improving lung health, physical performance and cardio-respiratory fitness, comprising administering in an effective amount a betacryptoxanthin composition comprising an extract enriched with trans-betacryptoxanthin to a subject undergoing exercise, wherein the extract comprises about 75 to 100% by weight of trans-betacryptoxanthin, wherein the amount is effective so as to reduce oxidative stress markers and increase antioxidant muscle enzymes in the subject undergoing exercise as compared to those of a subject that is undergoing exercise and has not been administered the betacryptoxanthin composition,
   wherein the administering comprises administering the trans-betacryptoxanthin in an amount of 1 to 2.5 mg/kg body weight of the subject,
   wherein the oxidative stress markers include lung and muscle malondialdehyde (MDA),
   wherein the lung and muscle antioxidant enzymes include at least one selected from the group consisting of superoxide dismutase (SOD) and glutathione peroxidase (GPx), and
   wherein the reduction of the oxidative stress markers and the increase of the antioxidant muscle enzymes are statistically significant.

2. The method of claim 1, wherein the reduction of the oxidative stress markers and the increase of the antioxidant muscle enzymes are statistically significant such that a p-value is 0.0001.

* * * * *